(12) United States Patent
Anderson

(10) Patent No.: US 8,968,398 B2
(45) Date of Patent: Mar. 3, 2015

(54) PRE-LOADED IOL INSERTION SYSTEM

(71) Applicant: Abbott Medical Optics Inc., Santa Ana, CA (US)

(72) Inventor: Steven R. Anderson, Rancho Santa Margarita, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/198,889

(22) Filed: Mar. 6, 2014

(65) Prior Publication Data

US 2014/0200589 A1    Jul. 17, 2014

Related U.S. Application Data

(62) Division of application No. 13/623,953, filed on Sep. 21, 2012, now Pat. No. 8,685,088, which is a division of application No. 12/144,512, filed on Jun. 23, 2008, now Pat. No. 8,273,122.

(51) Int. Cl.
*A61F 2/16* (2006.01)

(52) U.S. Cl.
CPC ............... *A61F 2/167* (2013.01); *A61F 2/1664* (2013.01); *A61F 2/1691* (2013.01)
USPC ........................................................ 623/6.12

(58) Field of Classification Search
CPC ..... A61F 2/1678; A61F 2/1672; A61F 2/167; A61F 2/1667; A61F 2/1664; A61F 2/1662
USPC .................. 606/107, 108; 623/6.11, 6.12
See application file for complete search history.

(56) References Cited

U.S. PATENT DOCUMENTS 4,619,656 A  *  10/1986  Lindstrom ................... 623/6.12
4,681,102 A      7/1987  Bartell
(Continued)

FOREIGN PATENT DOCUMENTS

BE        1016692 A3    4/2007
EP         722292 B1    7/2003
(Continued)

OTHER PUBLICATIONS

International Search Report and Written Opinion, mailed Nov. 5, 2009, and International Preliminary Report on Patentability, mailed Jan. 5, 2011, for Application No. PCT/US2009/048305, 15 pages.

*Primary Examiner* — Jonathan W Miles
(74) *Attorney, Agent, or Firm* — Abbott Medical Optics Inc.

(57) ABSTRACT

A system for easily transferring an intraocular lens (IOL) from an inserter into a patient's eye. The system includes an inserter handpiece with a holding station for receiving or storing an IOL. The IOL may be pre-loaded within the holding station during manufacture, and the inserter handpiece coupled to a delivery tube so that the entire system is ready for use by a surgeon to implant an IOL. The IOL may have an optic and leading and trailing haptics coupled to the optic, and the holding station may be capable of manipulating the haptics as desired to facilitate transfer of the IOL through the delivery tube into the eye. For instance, the holding station may fold one or both of the haptics over the optic. Preferably, the holding station maintains the haptics in their folded positions during transfer of the IOL into the delivery tube. The holding station desirably maintains the IOL in a relaxed configuration during storage. A small opening on one side may be provided to introduce a narrow tool for folding one of the haptics over the optic.

5 Claims, 10 Drawing Sheets

(56) References Cited

U.S. PATENT DOCUMENTS

| | | | |
|---|---|---|---|
| 4,702,244 A | 10/1987 | Mazzocco | |
| 5,066,297 A | 11/1991 | Cumming | |
| 5,171,241 A * | 12/1992 | Buboltz et al. | 606/1 |
| 5,275,604 A | 1/1994 | Rheinish et al. | |
| 5,304,182 A * | 4/1994 | Rheinish et al. | 606/107 |
| 5,494,484 A | 2/1996 | Feingold | |
| 5,496,328 A | 3/1996 | Nakajima et al. | |
| 5,499,987 A | 3/1996 | Feingold | |
| 5,578,042 A | 11/1996 | Cumming | |
| 5,616,148 A | 4/1997 | Eagles et al. | |
| 5,620,450 A | 4/1997 | Eagles et al. | |
| 5,630,841 A * | 5/1997 | McDonald | 128/898 |
| 5,728,102 A | 3/1998 | Feingold et al. | |
| 5,766,181 A | 6/1998 | Chambers et al. | |
| 5,772,666 A | 6/1998 | Feingold et al. | |
| 5,776,138 A * | 7/1998 | Vidal et al. | 606/107 |
| 5,800,442 A | 9/1998 | Wolf et al. | |
| 5,807,400 A | 9/1998 | Chambers et al. | |
| 5,860,984 A | 1/1999 | Chambers et al. | |
| 5,868,751 A | 2/1999 | Feingold | |
| 5,873,879 A | 2/1999 | Figueroa et al. | |
| 5,876,406 A | 3/1999 | Wolf et al. | |
| 5,876,440 A | 3/1999 | Feingold | |
| 5,891,152 A | 4/1999 | Feingold | |
| 5,902,307 A | 5/1999 | Feingold et al. | |
| 5,928,245 A | 7/1999 | Wolf et al. | |
| 5,941,886 A | 8/1999 | Feingold | |
| 5,947,975 A | 9/1999 | Kikuchi et al. | |
| 5,947,976 A | 9/1999 | Van et al. | |
| 6,001,107 A | 12/1999 | Feingold | |
| 6,010,510 A | 1/2000 | Brown et al. | |
| 6,022,358 A * | 2/2000 | Wolf et al. | 606/107 |
| 6,048,347 A | 4/2000 | Erdman | |
| 6,048,348 A | 4/2000 | Chambers et al. | |
| 6,056,757 A | 5/2000 | Feingold et al. | |
| 6,059,791 A | 5/2000 | Chambers | |
| 6,129,733 A | 10/2000 | Brady et al. | |
| 6,143,001 A | 11/2000 | Brown et al. | |
| 6,203,549 B1 | 3/2001 | Waldock | |
| 6,228,094 B1 | 5/2001 | Erdman | |
| 6,283,976 B1 | 9/2001 | Portney | |
| 6,312,433 B1 | 11/2001 | Butts et al. | |
| 6,336,932 B1 * | 1/2002 | Figueroa et al. | 606/107 |
| 6,371,960 B2 | 4/2002 | Heyman et al. | |
| 6,387,101 B1 | 5/2002 | Butts et al. | |
| 6,406,481 B2 | 6/2002 | Feingold et al. | |
| 6,468,282 B2 | 10/2002 | Kikuchi et al. | |
| 6,491,697 B1 | 12/2002 | Clark et al. | |
| 6,506,195 B2 | 1/2003 | Chambers et al. | |
| 6,537,283 B2 | 3/2003 | Van Noy | |
| 6,558,395 B2 | 5/2003 | Hjertman et al. | |
| 6,666,871 B2 | 12/2003 | Kikuchi et al. | |
| 6,723,104 B2 | 4/2004 | Ott | |
| 6,733,507 B2 | 5/2004 | McNicholas et al. | |
| 6,786,911 B2 | 9/2004 | Mitomo et al. | |
| 6,858,033 B2 | 2/2005 | Kobayashi | |
| 6,921,405 B2 | 7/2005 | Feingold et al. | |
| 7,014,641 B2 | 3/2006 | Kobayashi et al. | |
| 7,025,782 B2 | 4/2006 | Kobayashi et al. | |
| 7,037,312 B2 | 5/2006 | Kikuchi et al. | |
| 7,131,976 B2 | 11/2006 | Kobayashi et al. | |
| 7,156,854 B2 * | 1/2007 | Brown et al. | 606/107 |
| 7,229,449 B2 * | 6/2007 | Jeannin et al. | 606/107 |
| 7,276,071 B2 | 10/2007 | Lin et al. | |
| 7,303,582 B2 | 12/2007 | Brady | |
| 7,422,604 B2 | 9/2008 | Vaquero et al. | |
| 7,429,263 B2 | 9/2008 | Vaquero et al. | |
| 7,494,505 B2 * | 2/2009 | Kappelhof et al. | 623/6.12 |
| 8,273,122 B2 * | 9/2012 | Anderson | 623/6.12 |
| 8,435,289 B2 * | 5/2013 | Cole et al. | 623/6.12 |
| 8,685,088 B2 * | 4/2014 | Anderson | 623/6.12 |
| 2001/0007942 A1 | 7/2001 | Kikuchi et al. | |
| 2002/0156486 A1 | 10/2002 | Nadel | |
| 2002/0193805 A1 | 12/2002 | Ott et al. | |
| 2003/0045930 A1 | 3/2003 | Nguyen | |
| 2003/0187455 A1 | 10/2003 | Kobayashi et al. | |
| 2003/0212407 A1 | 11/2003 | Kikuchi et al. | |
| 2004/0199174 A1 * | 10/2004 | Herberger et al. | 606/107 |
| 2004/0243141 A1 * | 12/2004 | Brown et al. | 606/107 |
| 2005/0125000 A1 | 6/2005 | Tourrette et al. | |
| 2006/0184181 A1 | 8/2006 | Cole et al. | |
| 2008/0033449 A1 * | 2/2008 | Cole et al. | 606/107 |
| 2008/0058830 A1 | 3/2008 | Cole et al. | |
| 2008/0065096 A1 * | 3/2008 | Kappelhof et al. | 606/107 |
| 2008/0097459 A1 | 4/2008 | Kammerlander et al. | |
| 2008/0114313 A1 | 5/2008 | Gomez et al. | |
| 2010/0217273 A1 | 8/2010 | Someya et al. | |

FOREIGN PATENT DOCUMENTS

| | | |
|---|---|---|
| EP | 743840 B1 | 7/2003 |
| EP | 1338254 A1 | 8/2003 |
| EP | 1502559 A1 | 2/2005 |
| EP | 1360944 B1 | 9/2007 |
| EP | 2161005 A1 | 3/2010 |
| EP | 1737393 B1 | 6/2010 |
| EP | 2123239 B1 | 3/2012 |
| JP | 4707016 B2 | 6/2011 |
| WO | WO-9524863 A1 | 9/1995 |
| WO | WO-9615743 A1 | 5/1996 |
| WO | WO-9937247 A1 | 7/1999 |
| WO | WO-0187187 A1 | 11/2001 |
| WO | WO-03024354 A2 | 3/2003 |
| WO | WO-2004105648 A1 | 12/2004 |
| WO | WO-2004105649 A1 | 12/2004 |
| WO | WO-2005020553 A2 | 3/2005 |
| WO | WO-2005930097 A1 | 4/2005 |
| WO | WO-2005070341 A1 | 8/2005 |
| WO | WO-2008014260 A1 | 1/2008 |
| WO | WO-2008060869 A2 | 5/2008 |

* cited by examiner

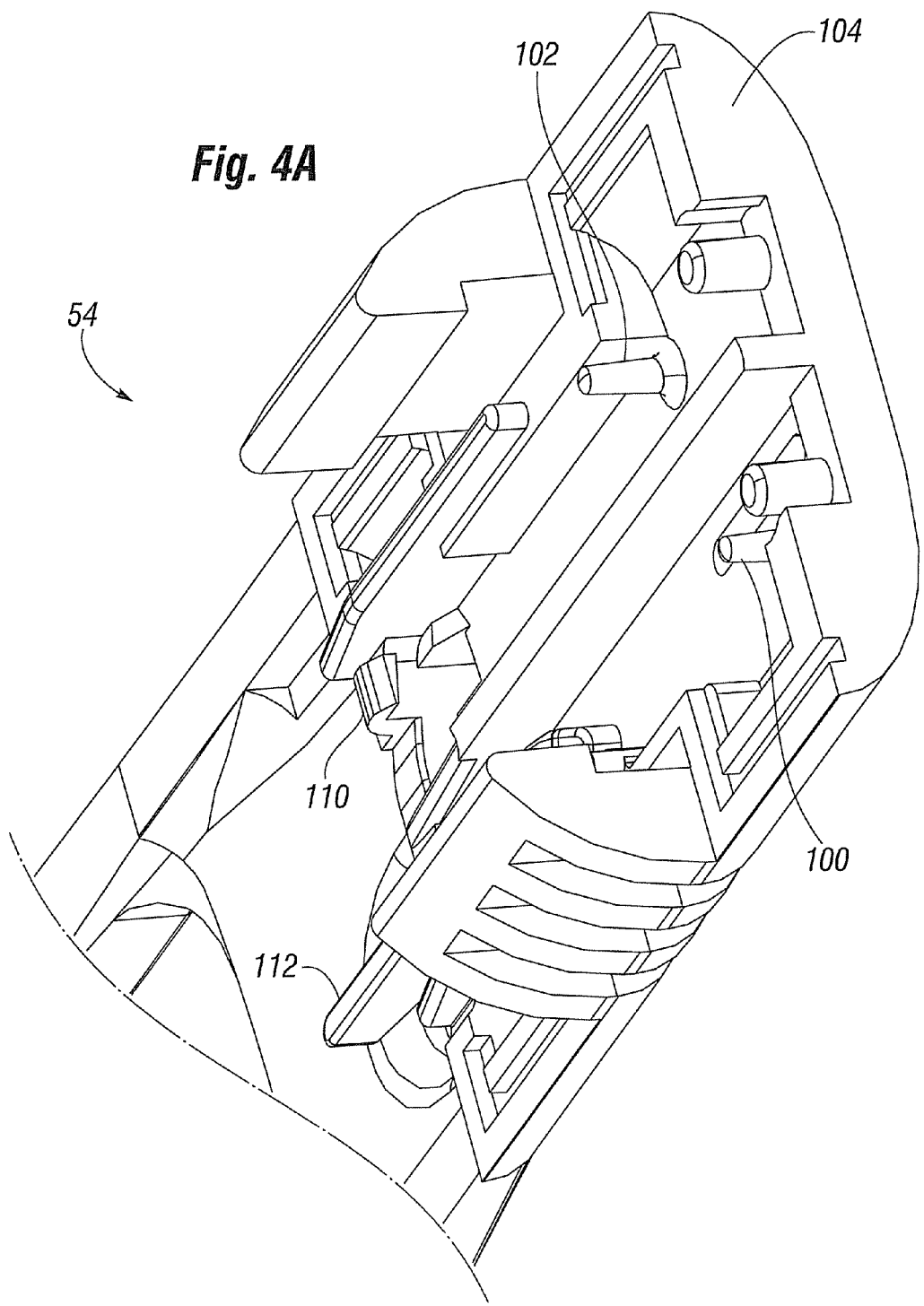

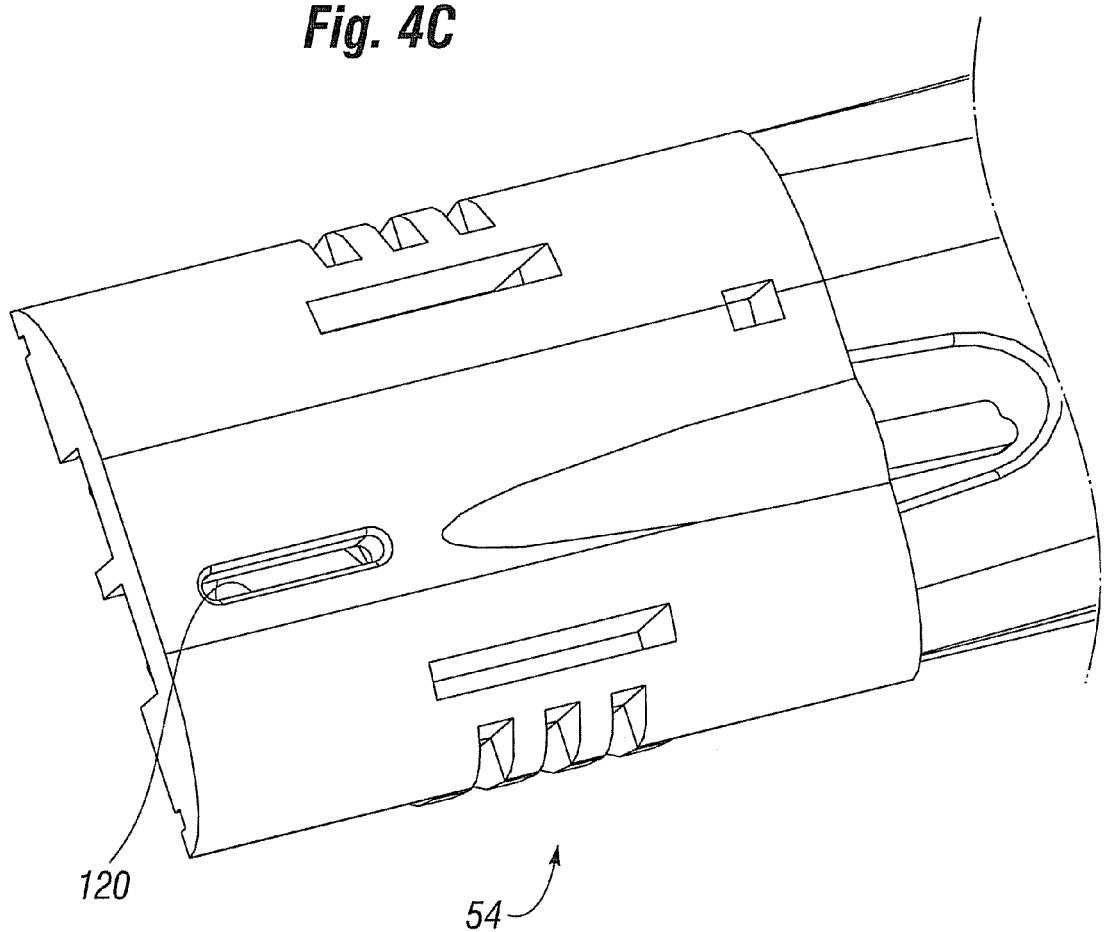

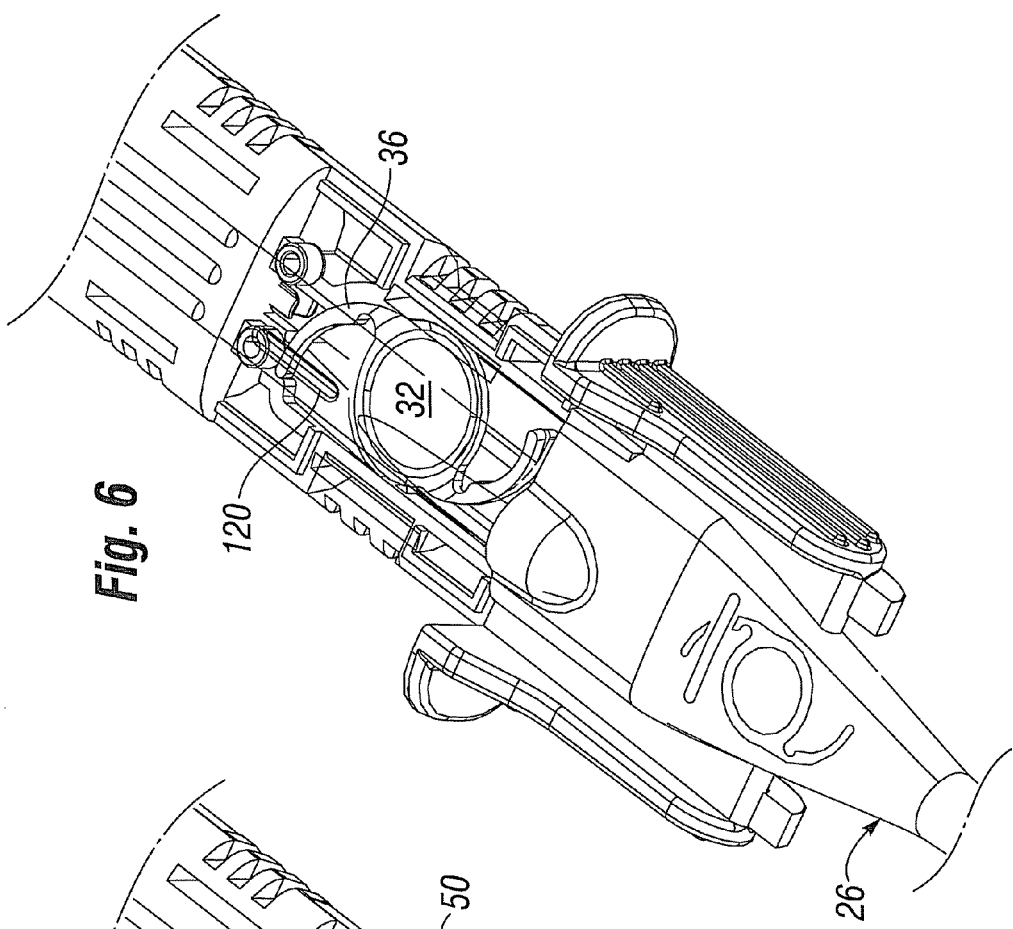
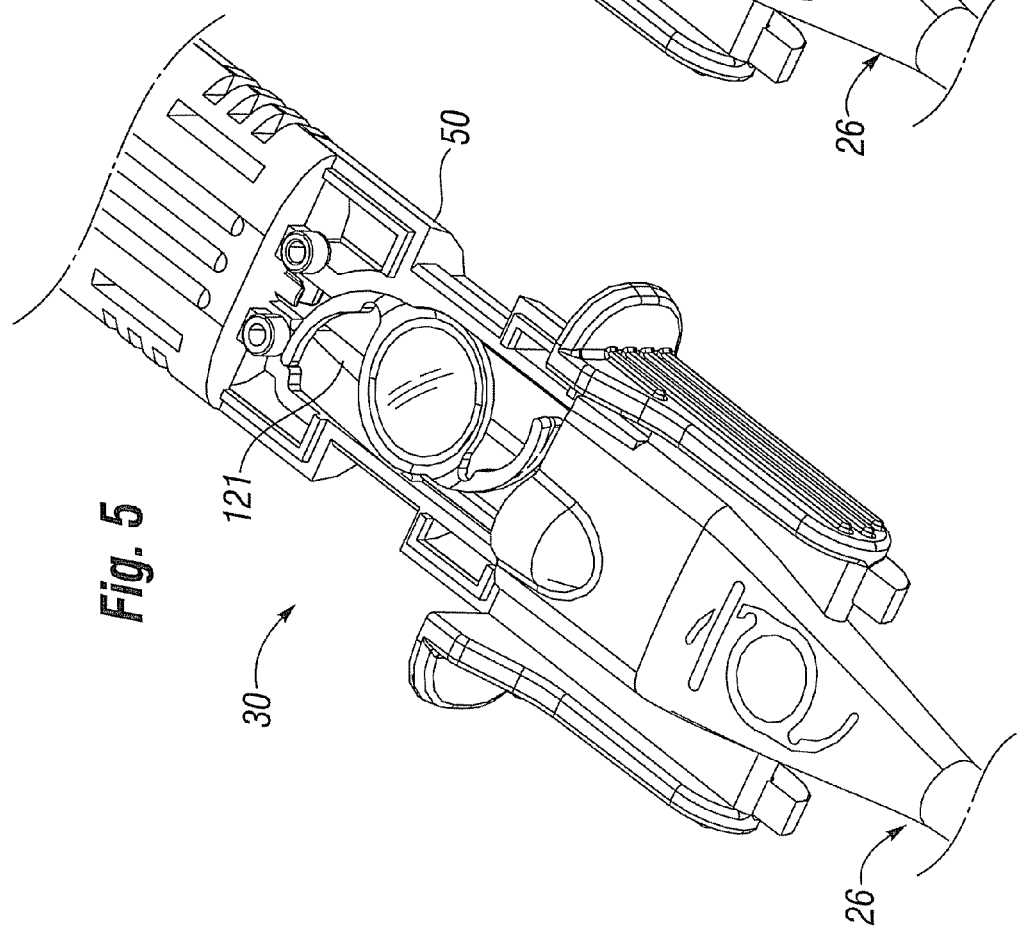

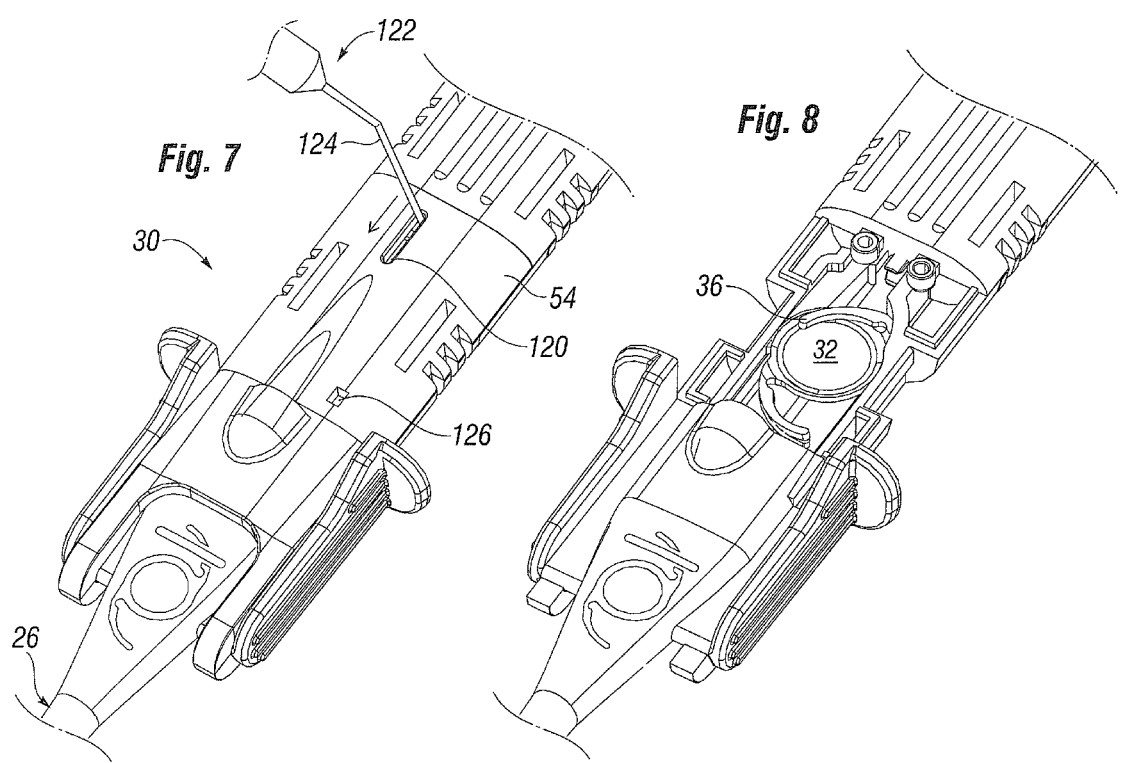

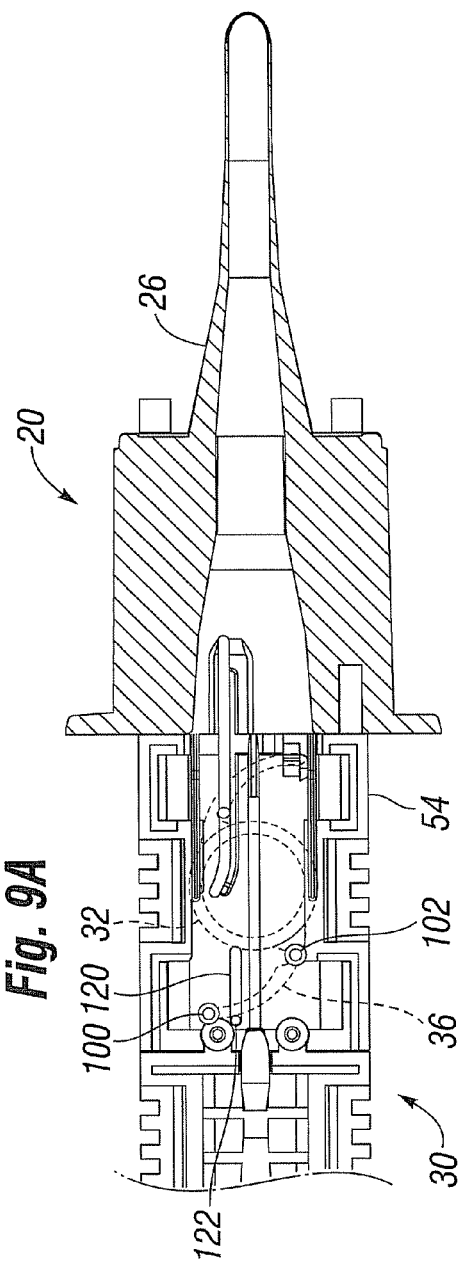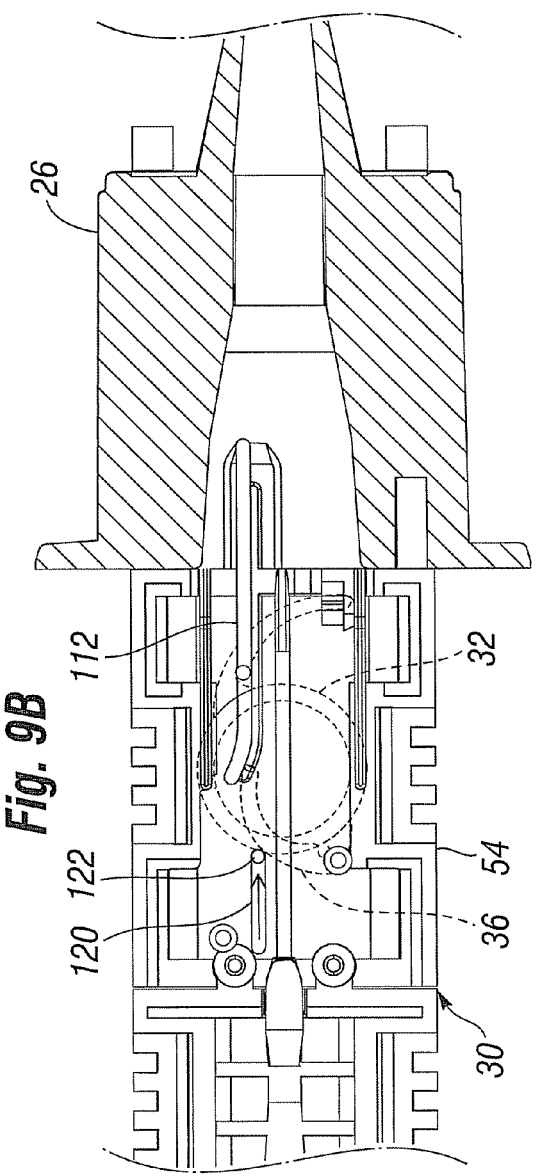

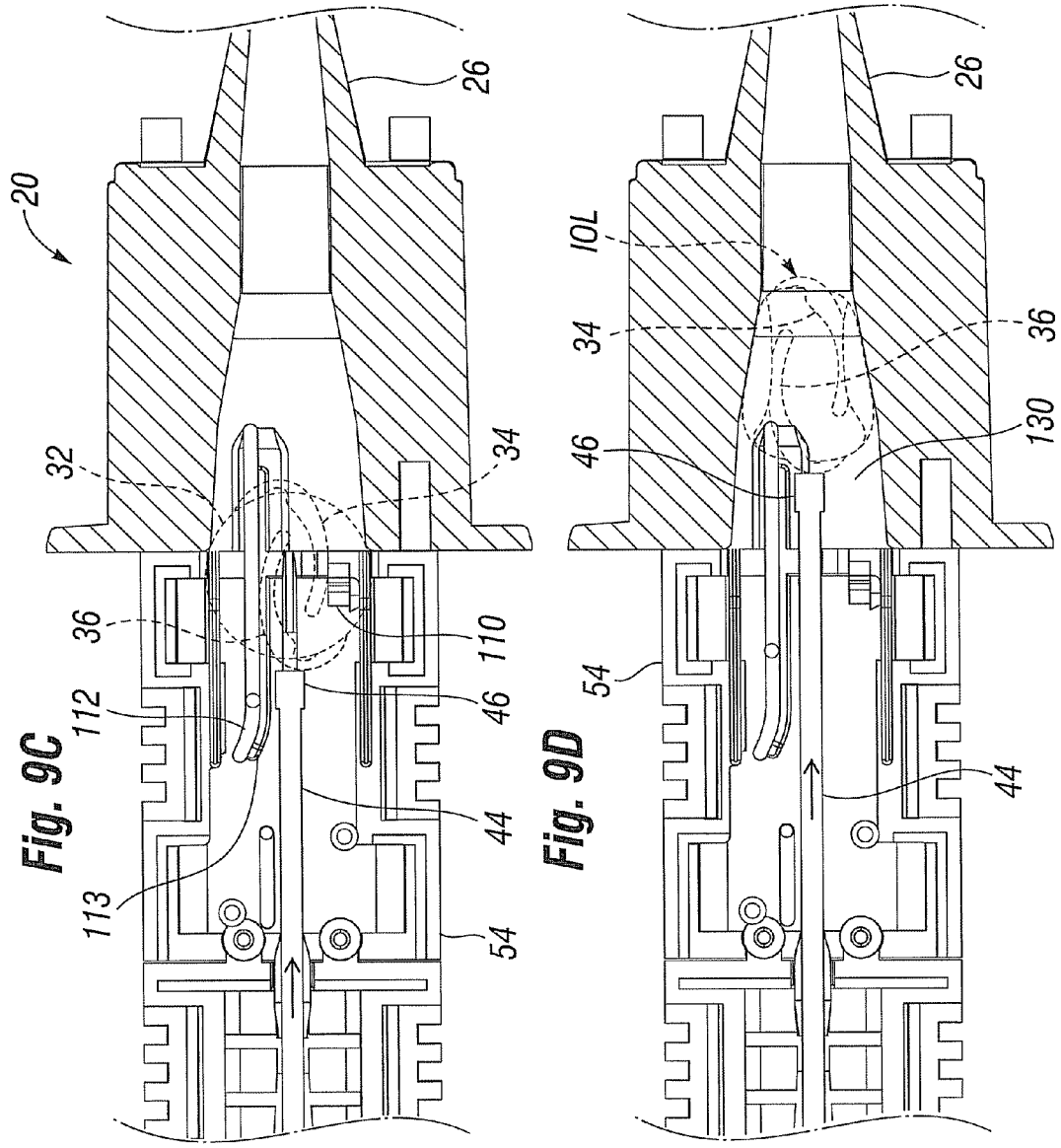

PRE-LOADED IOL INSERTION SYSTEM

RELATED APPLICATIONS

This application is a divisional application of and claims priority to U.S. application Ser. No. 13/623,953 filed on Sep. 21, 2012, which is a divisional application of and claims priority to U.S. application Ser. No. 12/144,512 filed on Jun. 23, 2008, now U.S. Pat. No. 8,273,122, both of which are hereby incorporated by reference in their entirety.

FIELD OF THE INVENTION

The present invention relates to devices, systems, and methods for delivering an intraocular lens into an eye. More particularly, the invention relates to devices, systems, and methods in which the intraocular lens is loaded into the front end of the device.

BACKGROUND OF THE INVENTION

It is estimated that 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded natural crystalline lens is removed and replaced with an intraocular lens (IOL) implant.

Surgeons implant IOLs not only as a replacement for the natural crystalline lens but also to alter the optical properties of (provide vision correction to) an eye in which the natural lens remains. IOLs often include an optically clear disk-like optic of about 6 mm in diameter, and preferably at least one flexible fixation member or haptic which extends radially outward from the optic and becomes affixed in the eye to secure the lens in position.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through an injector or insertion cartridge and an incision into the eye. Once within the chamber of the eye, the IOL is expulsed from the injector and returns to its original shape.

Injectors or inserters for delivering IOLs into the eye typically employ a handpiece and a removable cartridge that receives the IOL and has a hollow insertion tube or cannula through which the folded IOL is passed using a push rod. Some inserters do without the cartridge. The inserter may be wholly or partly reusable, in which case the inserter or handpiece is usually made of some type of metal alloy that can be sterilized. Alternatively, disposable inserters made of less expensive materials, such as plastics, remain in a sterile package until ready for use. In all cases, the IOL is stored separately and transferred to a load chamber in the inserter or cartridge just prior to delivery. One particularly useful arrangement wherein the cartridge folds over an IOL is disclosed in U.S. Pat. No. 4,681,102 to Bartell. A cartridge opens to receive an IOL in a load chamber, and then folds closed and fits into an injector. A syringe-like plunger in the injector pushes the IOL from the load chamber through a tapered tube into the eye. The IOL unfolds as it emerges from the tip of the tapered tube. Another such insertion system is disclosed in Makker et al., U.S. Pat. No. 5,942,277.

One problem encountered with existing inserters is difficulty in loading the IOL into the inserter or cartridge. The IOL is typically manually moved from a sterile environment to an inserter or associated cartridge using forceps or tweezers. Manual transfer of the IOL presents difficulties in maintaining both sterility of the IOL and the correct orientation of the IOL, especially the haptics, within the cartridge or inserter. A wide variety of performance and outcomes results even with highly skilled personnel, and those having less training are more likely to perform poorly. Improper orientation of the IOL can result in inadequate surgeon control and even damage to the IOL during delivery into the eye.

These problems may be mitigated by preloading the IOL at the manufacturer into a cartridge or container that is designed to be included directly in the inserter. The cartridge or container may be attached to the inserter either at the manufacturer or by the user just prior to surgery. The IOL is stored directly in the inserter in an unstressed state in a sterile package in order to prevent deformation of the optic element. A transfer process is not generally necessary for loading the IOL into the inserter. One example of storing an IOL in an inserter component is seen in U.S. Pat. No. 7,156,854, filed May 28, 2003. In the '854 patent, a nozzle portion 12 along with a removable stop 26 retains the IOL therein during storage and has internal ramps that assist in folding the IOL optic during an implant procedure. Also, U.S. Patent Publication No. 2008-0058830, filed Jul. 17, 2007, discloses a number of configurations for pre-loading IOLs for transfer to an insertion apparatus, and is expressly incorporated herein.

Despite some advances in this area, there remains a need for devices, systems, and methods that facilitate the placement of IOLs into an inserter or cartridge to reduce the problems associated with manual IOL manipulation.

SUMMARY OF THE INVENTION

The present invention relates to devices, systems, and methods for delivering an intraocular lens into the eye of a subject or patient that addresses at least some of the problems discussed above.

In accordance with one aspect of the invention, a system for delivering an intraocular lens (IOL) into the eye of a subject comprises an IOL having an optic, a leading haptic, and a trailing haptic. An IOL insertion system has a handpiece defining therein a holding station for receiving the IOL, the holding station including internal features that contact the leading and trailing haptics. An actuator displaces the IOL from the holding station in a distal direction along an axis, wherein one of the internal features of the holding station folds the leading haptic across the optic as the IOL is displaced in the distal direction. Also, a delivery tube has a proximal end open to the holding station along the axis to receive the IOL displaced by the actuator. The delivery tube defines a load chamber into which the IOL first enters, and the load chamber has dimensions that prevent unfolding of haptics.

Preferably, the holding station further includes an opening to the exterior thereof and passing over the trailing haptic of the IOL. The holding station may have a base and a cover that are hingedly connected and which may be unfolded for receiving an IOL therein. Also, the hinged base and cover may define a cavity that is sized to receive and retain the delivery tube such that the open proximal end thereof registers with an open distal end of the holding station, wherein the delivery tube and IOL are captured upon closure of the hinged base and cover. In a preferred embodiment, the actuator comprises a rod that translates linearly through the holding station and a substantial portion of the delivery tube. Furthermore, one of the internal features that contacts the trailing haptic may be a deflector rail that projects into the load chamber of the delivery tube.

The present invention also defines a method of packaging and delivering an IOL having an optic and leading and trailing haptics to a patient's eye. The method includes pre-loading an IOL in an insertion system, in that the IOL is packaged with the insertion system. The insertion system has a handpiece defining therein an IOL holding station for receiving the IOL, and an actuator adapted to displace the IOL from the holding station in a distal direction. The insertion system further includes a delivery tube adjacent the IOL holding station having an open proximal end for receiving the IOL displaced by the actuator. The method involves inserting a tool through an opening in the JUL holding station and manually repositioning a trailing haptic of the IOL over the IOL optic. The actuator displaces the IOL in the distal direction, and the IOL holding station has internal features that reposition the leading haptic of the IOL over the IOL optic and maintain the trailing haptic positioned over the IOL optic as the IOL is displaced. Finally, the delivery tube has an internal load chamber shaped to receive the IOL from the holding station and maintain the leading and trailing haptics positioned over the IOL optic. In the aforementioned method, the opening is desirably sized to receive a cannula of a viscoelastic applicator. A retaining pin may extend from the holding station into contact with the IOL to prevent movement of the JUL during repositioning of the trailing haptic of the IOL over the IOL optic. The internal feature that maintains the trailing haptic positioned over the IOL optic may be a deflector rail that projects into the load chamber of the delivery tube. The actuator preferably includes a detent feature that signifies to a user when the actuator has displaced the IOL into the load chamber, and the method includes displacing the IOL into the load chamber until the detent signifies its position, pausing, and then displacing the IOL farther through the delivery tube into a patient's eye.

Another aspect of the invention is an IOL insertion system, comprising a handpiece, a delivery tube, and an actuator. The handpiece defines a holding station which comprises a base for receiving an IOL and a cover that fits over the base and structure for contacting the IOL. The cover is hinged to the base to enable the cover to be open for introduction of the IOL to the base, and folded closed to capture the IOL and/or the delivery tube. The holding station further includes an open distal end. The delivery tube has an open proximal end and a distal tapered end. An exterior of the delivery tube is sized and shaped to fit within a cavity defined by the hinged holding station cover and base such that closing the cover over the base also captures the delivery tube with the open proximal end thereof in registration with the open distal end of the holding station. The actuator is adapted to displace the IOL from the holding station in a distal direction into the open proximal end of the delivery tube. In one embodiment, the system consists at most of five separate parts: the delivery tube, the handpiece in one or two parts, the actuator; and an O-ring that fits in the handpiece and damps movement of the actuator. The holding station may include an internal deflector member that contact and folds the leading haptic across the optic as the IOL is displaced in the distal direction. Desirably, the delivery tube has a load chamber into which the IOL first enters, the load chamber having dimensions that prevent unfolding of leading haptic. Preferably, the holding station includes an internal deflector rail and an opening to the exterior thereof and passing over the trailing haptic of the IOL, wherein a tool may be inserted in the opening to fold the trailing haptic over the IOL optic into contact with the deflector rail. In one embodiment the deflector rail extends into the open proximal end of the delivery tube and maintains the trailing haptic folded over the IOL optic as the IOL is displaced in the distal direction into the delivery tube.

The present invention also provides a method of assembling an IOL insertion system, comprising providing a handpiece defining therein a holding station for receiving the IOL. The holding station has a base for receiving an IOL and a cover that fits over the base and including structure for contacting the IOL. The cover is hinged to the base to enable it to be folded open for introduction of the IOL to the base, and the holding station further includes an open distal end. A delivery tube is provided having an open proximal end and a distal tapered end. An exterior of the delivery tube is sized and shaped to fit within a cavity defined by the hinged holding station cover and base. The holding station cover is folded open, an IOL is placed in the holding station base, and the delivery tube is positioned in the cavity defined by the holding station. The holding station cover is then folded closed over the base to capture the IOL and the delivery tube between the cover and base with the open proximal end thereof in registration with the open distal end of the holding station.

The method may further include inserting a tool through an opening in the IOL holding station and manually repositioning a trailing haptic of the IOL over the IOL optic, wherein the opening is sized to receive a cannula of a viscoelastic applicator. The IOL may be displaced with a handpiece actuator through the holding station and delivery tube, the IOL holding station further including internal features that reposition the leading haptic of the IOL over the IOL optic as the IOL is displaced in the distal direction and maintain the trailing haptic positioned over the IOL optic. The method of assembly may be accomplished manually, or with the assistance of robotic or otherwise automated assembly equipment.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIGS. 4A-4C are several perspective views of a cover for a lens holding station of the insertion system of the present invention;

FIG. 5 is an upper perspective view of the lens holding station of the insertion system of the present invention showing an intraocular lens (IOL) positioned within a base and with the holding station cover removed;

FIG. 6 is the same perspective as FIG. 5 but with the holding station cover shown opaque;

FIG. 7 is the same perspective view as FIGS. 5 and 6 with the holding station cover shown solid and illustrating manipulation of a trailing haptic of the IOL with a tool;

FIG. 8 is a view similar to that of FIG. 6 but showing the position of the trailing haptic after having been folded over the optic of the IOL with the tool of FIG. 7; and FIGS. 9A-9D are horizontal cross-sections, looking upward along line 9-9 of FIG. 7, of an IOL in phantom within the insertion system of the present invention showing several steps in folding haptics of the IOL and transferring the IOL to a delivery tube.

DETAILED DESCRIPTION OF THE PREFERRED EMBODIMENTS

The present invention facilitates the process of delivering an intraocular lens (IOL) into a patient's eye using an inserter. The IOL is typically implanted using an injector that rolls, folds, or otherwise configures the lens for delivery through a small incision in the eye in a way that reduces trauma and expedites post-surgery healing. The IOL is stored and transferred to a funnel-shaped delivery tube just prior to delivery. The injector or injector/cartridge is generally used in a manner like a hypodermic needle, with the IOL being injected into the eye through a delivery tube. The injector, cartridge and/or delivery tube may be first partially filled with a liquid or gel lubricating agent, for example a viscoelastic material. These are commonly used techniques for delivering an IOL into a patient's eye, and the present invention will be described in the same context. However, it should be understood that certain principles of the present invention can apply to modified systems, such as those that do not use a syringe-style injector or a funnel-like delivery tube.

Moreover, the present invention provides a system in which an IOL is pre-loaded within an inserter component to eliminate the need to manually transfer the IOL from a separate package to an inserter or cartridge. The term pre-loaded means that the IOL is packaged with the insertion system, and not separately, which would require transfer of the IOL to the insertion system at the time of a surgical procedure. However, the present system may also be used with an IOL is package separately and combined with the inserter system after shipment and/or at the time of implant. Likewise, although various components may be molded together, these components can also be remotely separately and assembled. Also, the insertion systems described herein are especially suited for manipulating leading and trailing haptics of an IOL without the need for skill or training, but certain aspects of the present invention may be applicable to IOLs having haptics that do not require such manipulation. In general, the present invention should not be considered limited to particular IOL insertion configurations except as defined accordingly in the claims.

Figure 1:
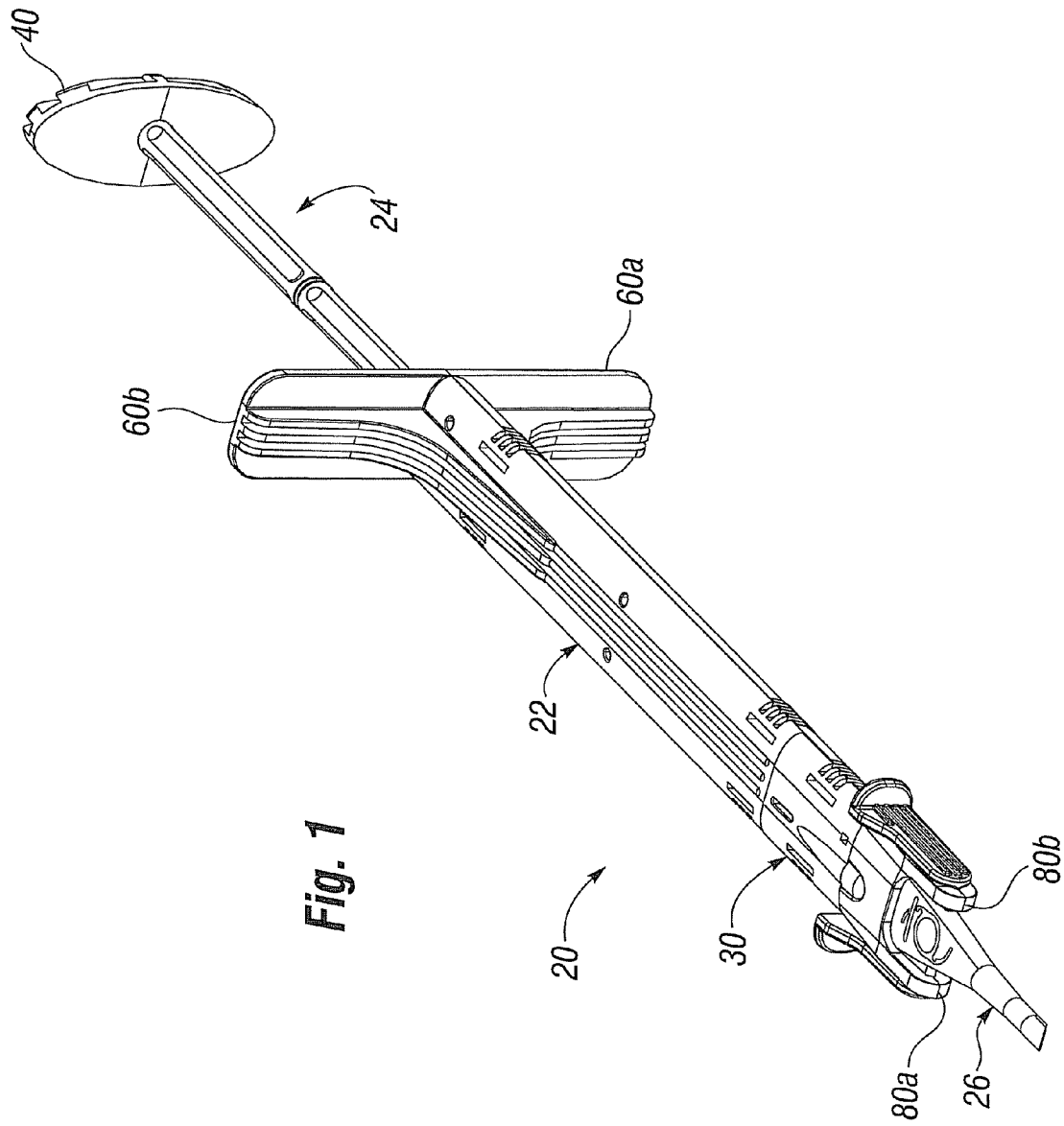
FIG. 1 is an assembled perspective view of an insertion system according to an embodiment of the invention.

FIG. 1 illustrates an exemplary IOL insertion system 20 of the present invention comprising a syringe-style device having, generally, a handpiece 22, a plunger 24, and a delivery tube 26 on a distal end thereof. The system 20 is also shown exploded in FIG. 2, and the handpiece 22 and plunger 24 components are shown exploded in FIG. 3 in a preferred mold configuration.

Figure 2:
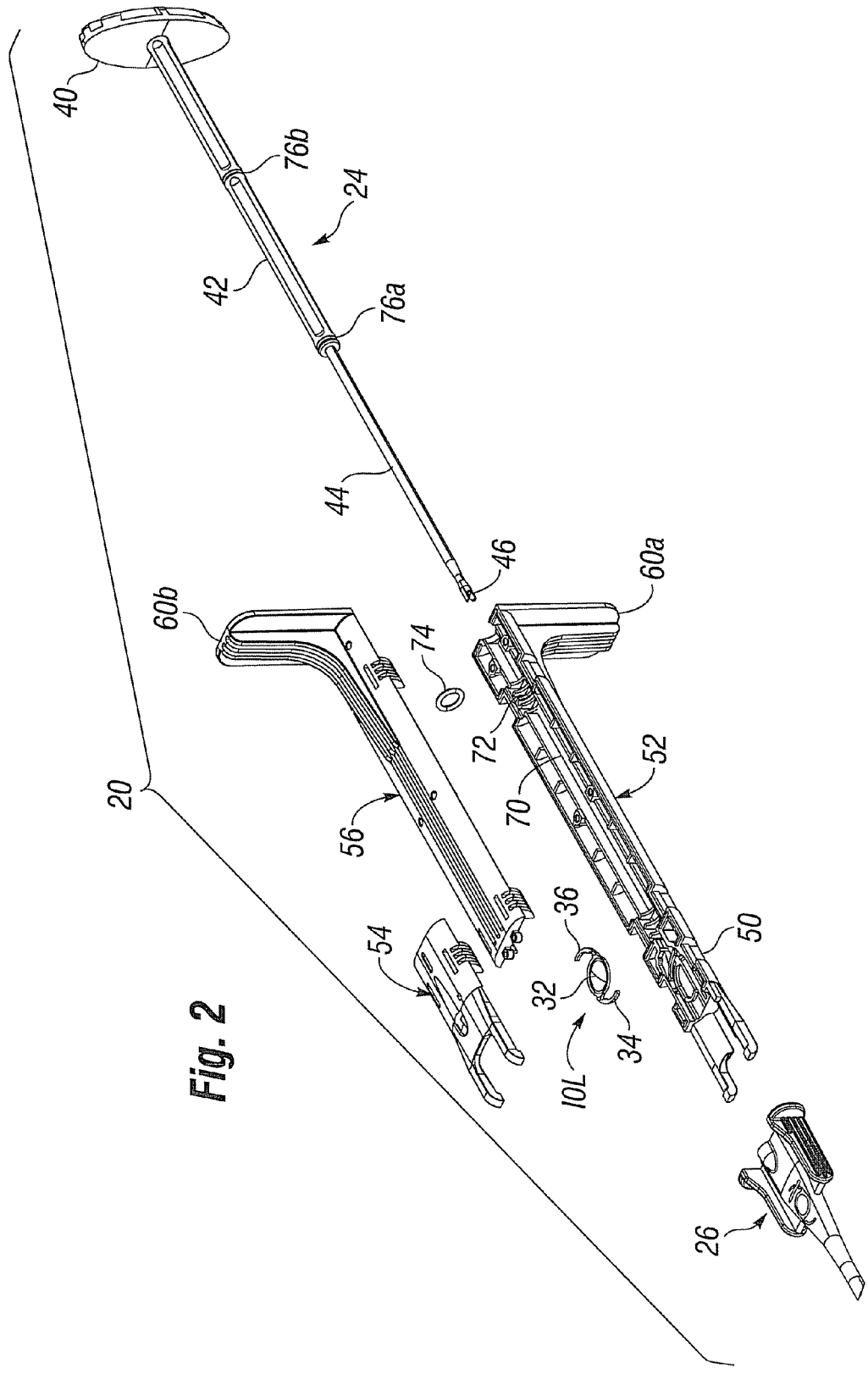
FIG. 2 is an exploded perspective view of the insertion system of FIG. 1.

The IOL is shown in FIG. 2 positioned between two halves of a holding station 30. The TOL may comprise a central circular optic 32 having a leading haptic 34 and a trailing haptic 36 generally spirally extending therefrom. As mentioned above, the present invention is especially suited for manipulating this particular configuration of IOL, although certain aspects of the invention may be applicable to other IOLs. One exemplary IOL as illustrated is a one piece acrylic Tecnis® brand of aspheric IOL available from Advanced Medical Optics of Santa Ana, Calif.

With reference to FIGS. 1 and 2, the system 20 defines a longitudinal axis from the plunger 24 at a proximal end to the delivery tube 26 at a distal end. The plunger 24 includes a thumb cap 40, a piston rod 42, a narrower push rod 44 fixedly connected to and extending from the piston rod, and a distal tip 46. In the illustrated embodiment, the distal tip 46 is forked to enable reliable capture of a proximal edge of the IOL optic 32. The plunger 24 translates axially through an elongate passage defined within the inserter handpiece 22 and is configured to urge the IOL from a holding station 30 through the distal delivery tube 26. In a general sense, the plunger 24 represents any actuator capable of displacing the TOL from the holding station 30 in a distal direction through a delivery tube or other such device. The plunger 24 therefore may be generally termed an actuator so as to encompass other prime movers that can perform the same function, such as a rotary actuators, threaded actuators, levers, etc.

The lower half of the holding station 30 comprises a base 50 that, in a preferred embodiment, forms a distal extension of a base portion 52 of the handpiece 22. The upper half of the holding station 30 comprises a cover 54 that abuts a top portion 56 of the inserter handpiece 22. In the illustrated embodiment, as seen in FIG. 1, the cover 54 and top portion 56 fit directly over the base 50 and base portion 52 to form the elongated handpiece 22. The overall shape of handpiece 22 may be somewhat flattened in a plane parallel to the interface between the upper and lower components. For example, the handpiece 22 may be configured to have an external aspect ratio in a cross-sectional plane perpendicular to the longitudinal axis of at least 1.5, at least 2, or at least 2.5 over a predetermined length parallel to the longitudinal axis, the predetermined length being greater than 50 percent or greater than 75 percent of the total length of the handpiece 22. As seen in FIG. 2, the IOL optic 32 is positioned approximately at a horizontal midplane of the inserter handpiece 22, which plane also defines the orientation of handpiece.

The handpiece further includes a pair of proximal finger tabs 60a, 60b, one on the base portion 52 and one on the top portion 56. When an operator desires to depress the plunger 24, he or she places the thumb of one hand on the thumb cap 40, and index and middle fingers on respective finger tabs 60a, 60b. Squeezing the hand closed depresses the thumb cap 40. The flattened orientation of the inserter handpiece 22 may be ergonomically designed to lessen the profile between the index and middle fingers and thus enhance comfort. The flattened nature of the handpiece 22 also provides torque leverage so that the operator can more easily rotate the handpiece about its longitudinal axis.

The exploded view of FIG. 2 shows a central channel 70 in the handpiece base 52 for receiving the piston rod 42 and push rod 44. A similar mating channel is also provided on the underside of the handpiece top portion 56. A semi-circular groove 72 provided at the proximal end of the base 52 (and a similar mating groove on the underside of the top portion 56) receives an O-ring 74. The piston rod 42 includes two circular grooves 76a, 76b spaced along its length that register with the O-ring 74. Specifically, the piston rod 42 has an outer diameter slightly larger than the inner diameter of the O-ring 74, while the grooves 76a, 76b each have an outer diameter that is the same or approximately the same as the inner diameter of the O-ring. As the piston rod 42 passes through the proximal end of the handpiece 42 it spreads apart the O-ring 74 resulting in a degree of friction between plunger 24 and the handpiece 22, therefore damping of the movement of the piston rod 42 and/or the IOL. The O-ring 74 resiliently springs inward into each of the grooves 76a, 76b as they reach the proximal end of the handpiece. The grooves 76a, 76b and associated O-rings thus provide detents to movement of the plunger 24 through the handpiece 22.

The system 20 is packaged with the plunger 24 retracted and the distal groove 76a in registry with the O-ring 74. A technician or other user can prepare the system for an IUL insertion operation by applying the appropriate amount of a viscoelastic, manipulating the trailing haptic 36 as described below, and advancing the plunger 24 such that the proximal groove 76b registers with the O-ring 74. This positive position indicator notifies the user that the system 20 is ready for the surgeon. The plunger 24 remains out of contact, or just touches, the IOL.

FIG. 2 is an exploded view of the components of the system 20 in the orientation in which they will be assembled. However, a preferred mold configuration results in a total of five (or possibly fewer) components for the entire system, not counting the IOL. The five components include the plunger 24, the delivery tube 26, the O-ring 74, the handpiece top portion 56, and the remainder of the handpiece including the holding station 30 and base portion 52. It is possible that the handpiece top portion 56 could be formed along with the remainder of the handpiece, though the mold would be fairly complicated and expensive. Likewise, the delivery tube 26 could be incorporated into the handpiece 22, but again for reasons of manufacturing economy they are separate.

Figure 3:
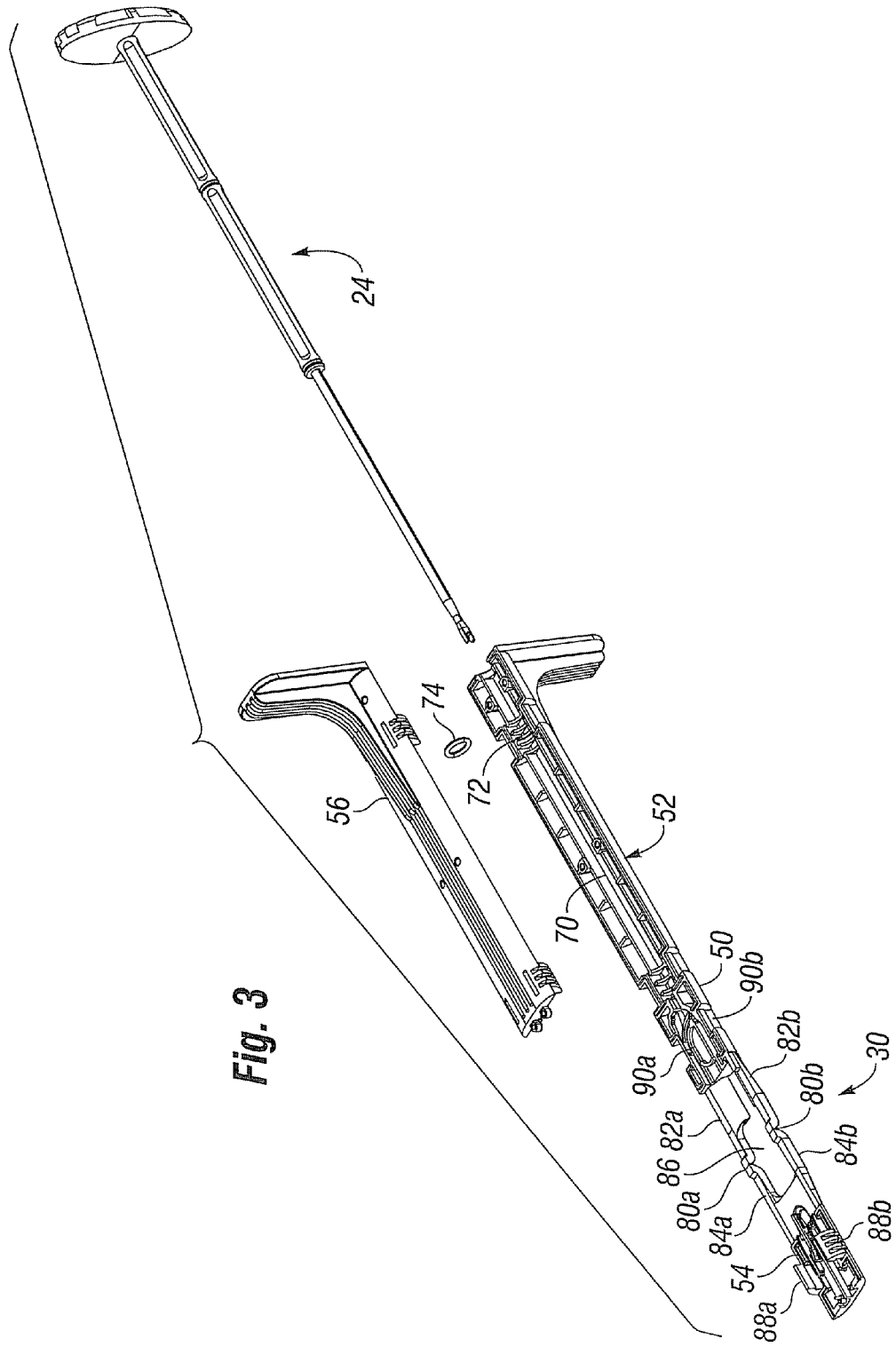
FIG. 3 is an exploded perspective view of an alternative insertion system similar to that shown in FIG. 2 but with a preferred final mold configuration.

The preferred mold configuration is seen in FIG. 3, with the holding station cover 54 connected by a pair of living hinges 80a, 80b to the base 50. The base 50 includes a pair of bifurcated fingers 82a, 82b that meet a similar pair of bifurcated fingers 84a, 84b extending from the cover 54 at the living hinges 80a, 80b. The opposed pairs of aligned fingers 82, 84 are shaped so as to form slots therebetween when folded about the living hinges 80 and a central cavity 86 for receiving a delivery tube 26, as best seen in the assembled view of FIG. 1. In this regard, the delivery tube 26 desirably comprises a rear-loading cartridge as shown, and as described in co-pending application Ser. No. 12/111,028, filed on Apr. 28, 2008, the contents of which are expressly incorporated herein.

As mentioned above, the present insertion system 20 advantageously enables pre-loading of an IOL so that manual handling is eliminated. As can be seen from the figures, assembly of the system may include placing an IOL in a shaped cavity in the holding station base 50 with the cover 54 folded open as shown in FIG. 3 (and see FIG. 5). Subsequently, a portion of, or the entire, delivery tube 26 is placed in the cavity 86 and the holding station cover 54 folded 180° about the hinges 80 over the top of the base 50. A pair of resilient latches 88a, 88b in the cover 54 snap around a pair of mating recesses 90a, 90b in the base 50 to lock the two components together. An open distal end of the holding station 30 communicates directly with an open proximal end of the delivery tube 26. The O-ring 74 is placed in the groove 72 and the handpiece top portion 56 snapped onto the base portion 52. Because of the preferred material, polypropylene, mechanical snaps or similar expedients are used to couple the parts together, although adhesives or other means may be used with other materials. Insertion of the plunger 24 into the proximal end of the channel 70 completes the assembly.

The IOL holding station 30 defines internal features that contact the leading and trailing haptics 34, 36 of the IOL to manipulate them during an implant procedure so that they are expelled from the delivery tube 26 in a controlled fashion. A wide of internal features are contemplated for contacting and controlling placement of the haptics 34, 36, and the following description of one embodiment should be considered exemplary only.

Figure 4B:
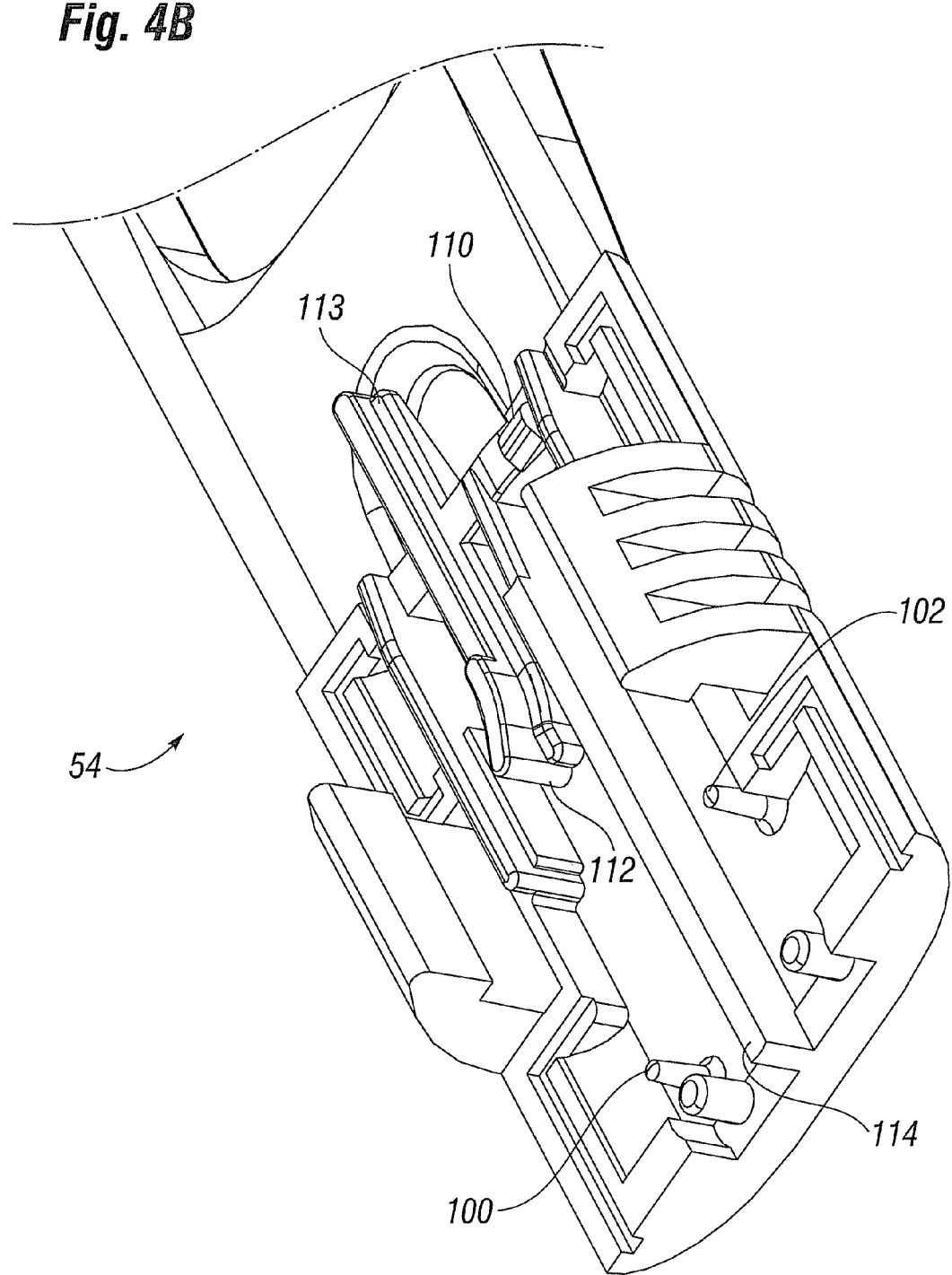

FIGS. 4A-4C illustrate detailed features of the holding station cover 54. After the IOL has been placed in the cavity in the base 50, and the cover 54 closed over the top of the base, a pair of retaining pins 100, 102 may be configured to contact the IOL and maintain the IOL in a desired orientation during an implant procedure, and also help maintain it in the cavity in the base during storage and/or shipment. One of the retaining pins 100, 102 may be configured to contact a tip of one of the haptics 34, 36, while another may contact the IOL optic 32. More specifically, the first retaining pin 100 may be located closer to a proximal end 104 of the cover 54 contacts the tip of the trailing haptic 36, and the second retaining pin 102 contacts an outer edge of the IOL optic 32 at a junction between the optic and the trailing haptic 36. These pins 100, 102 prevent rotation of the IOL during manipulation of the trailing haptic 36, as explained below.

The underside of the holding station cover 54 further includes internal features that contact and deform the leading and trailing haptics; namely, a leading haptic deflector member 110 and a trailing haptic deflector rail 112. The deflector member 110 and deflector rail 112 act on the leading and trailing haptics 34, 36 as the IOL translates through the holding station 30. The cover 54 further includes a central rib 114 that helps guide the distal tip 46 of the plunger 24 through the holding station 30.

Prior to movement of the IOL, however, the trailing haptic 36 may be folded over the top of the IOL optic 32, either manually or using an automated device. To accomplish that, the holding station cover 54 is provided with an opening, such as the slot 120 as seen in FIG. 4C located over the trailing haptic 36, through which a tool may be inserted to manipulate the haptic, as will be explained below.

FIG. 5 shows the IOL in its position within the cavity in the base 50 of the holding station 30 (the holding station cover 54 as been removed to illustrate the internal placement). FIG. 6 is the same view but showing a portion of the cover 54, and specifically the location of the slot-shaped opening 120. The opening 120 extends parallel to the longitudinal axis of the system 20 over the trailing haptic 36, from a point proximal to the trailing haptic 36 to a point over the IOL optic 32. As seen in FIG. 5, the base 50 may define a guide channel 121 opposite, parallel and co-extensive with the opening 120 in the cover 54.

Now with reference to FIG. 7, a tool 122 having a narrow elongated portion 124 may be inserted through the opening 120 to move the trailing haptic 36. In a preferred embodiment, the opening 120 is sized to receive a cannula of a viscoelastic applicator such as Healon® viscoelastic available from Advanced Medical Optics of Santa Ana, Calif. The viscoelastic applicator is commonly used during IOL insertions to lubricate the internal passages of the inserter and/or cartridge, and in this regard performs dual functions. In general, the opening 120 is sized to receive any hypotube-like applicator, such as the one illustrated. The tool 122 extends far enough such that tip of the elongated portion 124 fits within the guide channel 121 in the base 50. The guide channel 121 terminates short of the position of the IOL optic 32, and thus prevents contact between the tool and optic. FIG. 8 shows the position of the trailing haptic 36 after having been folded over the IOL optic 32 by the tool 122. This operation is extremely simple and does not require highly skilled personnel.

FIGS. 9A-9D are horizontal cross-sections looking upward at an IOL in phantom within the insertion system 20, showing several steps in folding the leading and trailing haptics 34, 36 of the IOL and transferring the IOL to the delivery tube 26. FIG. 9A illustrates the storage position of the IOL against the holding station cover 54. The precise positions of the retaining pins 100, 102 relative to the IOL are shown. Namely, the first retaining pin 100 contacts the tip of the trailing haptic 36, and the second retaining pin 102 contacts the junction between the optic 32 and the trailing haptic 36. The length of the retaining pins 100, 102 is such that they gently contact and press the IOL at these locations against the holding station base 50 (see FIG. 5). In the storage position as shown, the pins 100, 102 help maintain the optic 32 and trailing haptic 36 in the illustrated position. FIG. 9A also shows the opening 120 and the tool 122 therein.

Now with reference to FIG. 9B, the tool 122 is moved along the opening 120 so that a distal portion of the trailing haptic 36 touches or engages the deflector rail 112. The tool 122 acts on the proximal side of the trailing haptic 36 to bend it relative to the optic 32 and fold it over the top of the optic (under the optic in the illustration). The retaining pin 102 helps prevent movement of the optic 32, and especially prevented from popping upward. The opening 120 has a length such that the tool 122 causes the trailing haptic 36 to fold over the optic 32 and into contact with a curved portion of the deflector rail 112. The deflector rail 112 curves to accommodate rotation of the tip of the trailing haptic 36 into this position. At this point, the tool 122 can be removed without rebound of the trailing haptic 36 because of its contact with the deflector rail 112. The material of the IOL and haptics influences the rate of rebound, and acrylic IOLs, especially when cold, are relatively slow to spring back into their initial relaxed positions. However, even if the IOL is formed of a material with greater elastic rebound properties (e.g., silicone), the trailing haptic 36 remains constrained by the deflector rail 112.

In the configuration shown in FIG. 9B, the IOL is prepared for transfer from the holding station 30 to the delivery tube 26. As explained previously, the open distal end of the holding station 30 communicates with the open proximal end of the delivery tube 26. The trailing haptic 36 has been folded over the top of the IOL optic 32 by the tool 122. At this point, it will be appreciated that there may be a number of small apertures through the walls of the holding station 30 to permit application of a viscoelastic into the holding station and delivery tube 26. One such aperture 126 is shown in FIG. 9C.

Subsequently, the plunger 24 (FIG. 2) is depressed so that the distal tip 46 of the pushrod 44 enters the holding station 30 and contacts the proximal end of the IOL. As seen in FIG. 9C, the distal tip 46 acts on the trailing haptic 36 as well as the edge of the optic 32. The IOL is shown in a position after having been moved distally a short distance by the plunger 24. The leading haptic deflector member 110 contacts the leading haptic 34 and causes it to deflect relative to the optic 32. Ultimately, the leading haptic 34 will fold over the top of the optic in a similar manner as the trailing haptic 36. FIG. 9C also shows a slight further bending of the trailing haptic 36 as it cams along the deflector rail 112. FIG. 4B best shows the configuration of the deflector rail 112, which includes a small step 113 against which the trailing haptic 36 slides.

FIG. 9D shows the IOL having been transferred into a load chamber 130 of the delivery tube 26. The size of the chamber 130 is desirably smaller than the diameter of the IOL optic 32, and therefore acts on and causes the optic to curl upward into a "taco" shape. The transition of the optic 32 from its original planar configuration to a curled configuration prevents the haptics 34, 36 from elastically rebounding back to their original positions. In other words, the haptics 34, 36 are captured over the top of the IOL optic 32 by its curled configuration.

The system 20 is thus designed to transfer the pre-loaded IOL directly from the holding station 30 into the delivery tube 26, and in the process fold the haptics 34, 36 over the optic 32 and maintain each of them in that desirable position. The deflector member 110 folds the leading haptic 34 over the optic 32, and when the leading haptic passes the deflector member it is already substantially within the load chamber 130. Because of the relatively slow elastic rebound property of the IOL materials, the leading haptic 34 does not spring forward again immediately, and the IOL continues a short distance further until the optic 32 begins curling, at which point the leading haptic 34 cannot spring forward. In a similar way, the deflector rail 112 extends beyond the distal end of the main body of the holding station cover 54 and into the load chamber 130. The trailing haptic 36 remains constrained by the deflector rail 112 until the optic 32 is substantially within the load chamber 130. The deflector rail 112 therefore maintains the trailing haptic 36 folded over the optic 32 until such time as the optic begins curling, after which the trailing haptic cannot spring back.

FIG. 9D shows the IOL in its loaded configuration within the delivery tube 26. This position corresponds to the location of the plunger 24 when the proximal groove 76b on the plunger rod 42 registers with the O-ring 74 (see FIG. 2). In other words, the detent function of the proximal groove 76b signifies to a user that the IOL has been loaded within the delivery tube 26. At this stage, the system 20 is fully prepared for use by a surgeon in the delicate operation of transferring the IOL from the delivery tube 26 into an eye of a patient. The tapered or funnel-like configuration of the delivery tube 26 can be seen in FIG. 9D. The IOL eventually emerges from a distal tip 132, which is most often angled. Because the haptics 34, 36 remain folded over the optic 32, they are in predictable and controlled positions throughout this operation. After emerging from the distal tip 132, the haptics 34, 36 gradually rebound into their original substantially spiral shapes, as seen in FIG. 5.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of packaging and delivering an IOL having an optic and leading and trailing haptics to a patient's eye, comprising:

pre-loading an IOL in an insertion system, the insertion system having a handpiece defining therein an IOL holding station for receiving the IOL and an actuator adapted to displace the IOL from the holding station in a distal direction, the insertion system further including a delivery tube adjacent the IOL holding station having an open proximal end for receiving the IOL displaced by the actuator;

inserting a tool through an opening in the IOL holding station and manually repositioning a trailing haptic of the IOL over the IOL optic;

displacing the IOL with the actuator in the distal direction, the IOL holding station further comprising a first internal feature that repositions the leading haptic of the IOL over the IOL optic and a second internal feature maintains the trailing haptic positioned over the IOL optic as the IOL is displaced; and the delivery tube having an internal load chamber shaped to receive the IOL from the holding station and maintain the leading and trailing haptics positioned over the IOL optic.

2. The method of claim 1, wherein the opening is sized to receive a cannula of a viscoelastic applicator.

3. The method of claim 1, further including a retaining pin extending from the holding station into contact with the IOL to prevent movement of the IOL during repositioning of the trailing haptic of the IOL over the IOL optic.

4. The method of claim 1, wherein the second internal feature that maintains the trailing haptic positioned over the IOL optic comprises a deflector rail that projects into the load chamber of the delivery tube.

5. The method of claim 1, wherein the actuator includes a detent feature that signifies to a user when the actuator has displaced the IOL into the load chamber, the method including displacing the IOL into the load chamber until the detent signifies its position, pausing, then displacing the IOL farther through the delivery tube into a patient's eye.

* * * * *